(12) United States Patent
Suzuki et al.

(10) Patent No.: US 11,413,016 B2
(45) Date of Patent: Aug. 16, 2022

(54) ULTRASOUND PROBE AND ULTRASOUND DIAGNOSTIC APPARATUS

(71) Applicant: Konica Minolta, Inc., Tokyo (JP)

(72) Inventors: Kenji Suzuki, Tokyo (JP); Yuta Nakayama, Chiba (JP)

(73) Assignee: KONICA MINOLTA, INC., Tokyo (JP)

( * ) Notice: Subject to any disclaimer, the term of this patent is extended or adjusted under 35 U.S.C. 154(b) by 426 days.

(21) Appl. No.: 16/741,095

(22) Filed: Jan. 13, 2020

(65) Prior Publication Data
US 2020/0229791 A1 Jul. 23, 2020

(30) Foreign Application Priority Data

Jan. 18, 2019 (JP) .............................. JP2019-007259

(51) Int. Cl.
*G01N 29/24* (2006.01)
*A61B 8/00* (2006.01)
*G01N 29/06* (2006.01)
*G01N 29/44* (2006.01)

(52) U.S. Cl.
CPC ....... *A61B 8/4444* (2013.01); *G01N 29/0654* (2013.01); *G01N 29/245* (2013.01); *G01N 29/44* (2013.01); *G01N 2291/044* (2013.01); *G01N 2291/101* (2013.01)

(58) Field of Classification Search
CPC ............. A61B 8/4444; G01N 29/0654; G01N 29/245; G01N 29/44; G01N 2291/044; G01N 2291/101; B06B 1/0696; B06B 1/064
See application file for complete search history.

(56) References Cited

U.S. PATENT DOCUMENTS

| | | | |
|---|---|---|---|
| 2010/0327694 A1* | 12/2010 | Omote ................... | H03H 9/059 310/313 R |
| 2015/0141827 A1 | 5/2015 | Kiyose | |
| 2019/0268702 A1* | 8/2019 | Ogata .................... | H04R 1/403 |

FOREIGN PATENT DOCUMENTS

| EP | 2783760 A2 * | 10/2014 | ........... A61B 8/4483 |
|---|---|---|---|
| JP | 2015517752 A | 6/2015 | |

OTHER PUBLICATIONS

EPO, Extended European Search Report for the corresponding European Patent Application No. 20152040.0, dated Jun. 22, 2020.

* cited by examiner

*Primary Examiner* — Suman K Nath
(74) *Attorney, Agent, or Firm* — Lucas & Mercanti, LLP

(57) ABSTRACT

An ultrasound probe including: a circuit substrate (23) having a recess in a first region on the lower surface side; a buffer layer (400) composed of an insulating material on a second region different from the first region of circuit substrate (23); and an element array layer (22) including a first piezoelectric element (100) for ultrasound transmission formed in the first region of the circuit substrate (23) without the buffer layer (400), and a second piezoelectric element (200) for ultrasound reception formed in the second region of the circuit substrate (23) on the buffer layer (400). The first piezoelectric element (100) vibrates in a flexural vibration mode on the circuit substrate (23), and the second piezoelectric element (200) vibrates in a thickness vibration mode on the circuit substrate (23).

16 Claims, 11 Drawing Sheets

ULTRASOUND PROBE AND ULTRASOUND DIAGNOSTIC APPARATUS

CROSS REFERENCE TO RELATED APPLICATIONS

The disclosure of Japanese Patent Application No. 2019-007259 filed on Jan. 18, 2019, is incorporated herein by reference in its entirety.

BACKGROUND

Technical Field

The present disclosure relates to an ultrasound probe and an ultrasound diagnostic apparatus.

Description of the Related Art

An ultrasound probe with an ultrasound emission surface on which multiple ultrasound transducers are arranged has been known. In recent years, an ultrasound probe using a piezoelectric element (also referred to as a piezoelectric micromachined ultrasound transducer (pMUT)) achieved by micro electro mechanical systems (MEMS) technology has been developed as an ultrasonic transducer (see PTL 1, for example).

An ultrasound probe using a pMUT can transmit and receive ultrasound by vibrating a diaphragm having a piezoelectric body like a drum (flexural vibration), for example. The pMUT is advantageous in that it can be made finer than a piezoelectric element obtained by dividing bulk lead zirconate titanate (PZT) by dicing or the like and can therefore be made higher in frequency and higher in resolution, and it is suitable for forming a two-dimensional array of piezoelectric elements for generating three-dimensional images, and it can be made compact and thin. However, when the same flexural vibration is used for transmission and reception as in the conventional pMUT, a problem of narrow band arises and the available frequency is limited to the vicinity of the resonance frequency.

Japanese Unexamined Patent Application Publication (Translation of PCT Application) No. 2015-517752 (hereinafter, referred to as "PTL") 1 discloses a pMUT array structure in which a wide band is achieved by arranging multiple pMUTs having different resonance frequencies (see FIG. 7B of PTL 1).

However, in the ultrasound probe having the pMUT array structure disclosed in PTL 1, a deep valley (that is, a frequency band that becomes a dead band) is generated between resonance peaks, and the image quality of the ultrasound image may therefore be deteriorated. Moreover, since multiple resonance frequencies are mixed, the transmission/reception sensitivity of the ultrasound probe as a whole may be lowered.

SUMMARY

An object of the present disclosure, which has been made in view of the above problems, is to provide an ultrasound probe and an ultrasound diagnostic apparatus that can achieve high transmission/reception sensitivity over a wide frequency band.

To achieve at least one of the abovementioned objects, according to an aspect of the present invention, an ultrasound probe reflecting one aspect of the present invention comprises:

a circuit substrate;

a buffer layer formed in a second region different from a first region of an upper surface of the circuit substrate and composed of an insulating material; and an element array layer including a first piezoelectric element for ultrasound transmission formed in the first region of the circuit substrate without the buffer layer, and a second piezoelectric element for ultrasound reception formed in the second region of the circuit substrate on the buffer layer, wherein the circuit substrate has a recess in a region of a lower surface, the region corresponding to the first region, the first piezoelectric element vibrates in a flexural vibration mode on the circuit substrate, and the second piezoelectric element vibrates in a thickness vibration mode on the circuit substrate.

To achieve at least one of the abovementioned objects, according to another aspect of the present invention, an ultrasound probe reflecting one aspect of the present invention comprises:

a circuit substrate;

a buffer layer that is formed of an insulating material, and has a first thickness in a first region of an upper surface of the circuit substrate and has a second thickness in a second region different from the first region, the second thickness being greater than the first thickness; and an element array layer including a first piezoelectric element for ultrasound transmission formed in the first region of the circuit substrate on the buffer layer, and a second piezoelectric element for ultrasound reception formed in the second region of the circuit substrate on the buffer layer, wherein the circuit substrate has a recess in a region of a lower surface corresponding to the first region, the first piezoelectric element vibrates in a flexural vibration mode on the circuit substrate, and the second piezoelectric element vibrates in a thickness vibration mode on the circuit substrate.

To achieve at least one of the abovementioned objects, according to another aspect of the present invention, an ultrasound probe reflecting one aspect of the present invention comprises: the ultrasound probe described above.

BRIEF DESCRIPTION OF DRAWINGS

The advantageous and features provided by one or more embodiments of the invention will become more fully understood from the detailed description given hereinbelow and the appended drawings which are given by way of illustration only, and thus are not intended as a definition of the limits of the present invention.

DETAILED DESCRIPTION OF EMBODIMENTS

Figure 1:
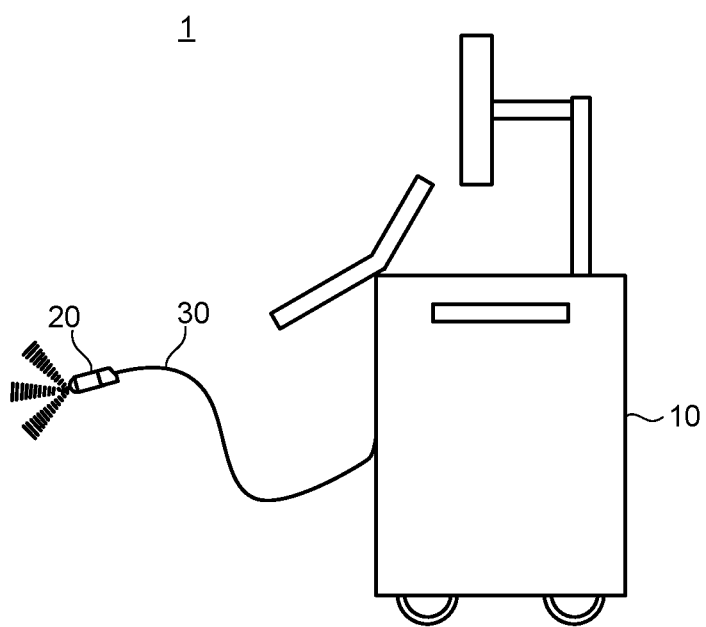
FIG. 1 is a diagram showing the appearance of an ultrasound diagnostic apparatus according to Embodiment 1.

Preferred embodiments of the present disclosure will now be described in detail with reference to the accompanying drawings. In this specification and drawings, components having substantially the same function are denoted by the same reference numerals, and redundant description is omitted.

Embodiment 1

Configuration of Ultrasound Diagnostic Apparatus

An example configuration of an ultrasound diagnostic apparatus according to this embodiment will now be described with reference to FIGS. 1 to 2.

Figure 2:
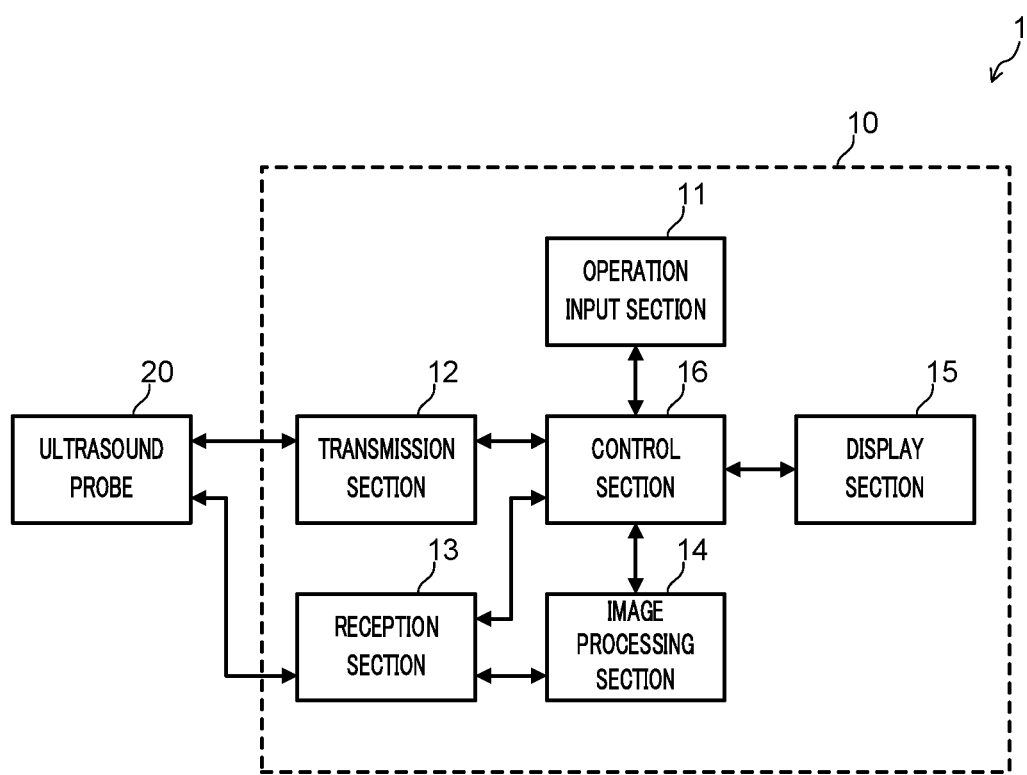
FIG. 2 is a block diagram showing the main part of the control system of the ultrasound diagnostic apparatus according to Embodiment 1.

FIG. 1 is a diagram showing the appearance of ultrasound diagnostic apparatus 1 according to this embodiment. FIG. 2 is a block diagram showing the main part of the control system of ultrasound diagnostic apparatus 1 according to this embodiment.

As shown in FIG. 1, ultrasound diagnostic apparatus 1 includes ultrasound diagnostic apparatus body 10 and ultrasound probe 20. Ultrasound diagnostic apparatus body 10 and ultrasound probe 20 are connected via cable 30.

Ultrasound diagnostic apparatus 1 is used for visualizing the shape, properties, or dynamics in a subject in an ultrasound image and performing image diagnosis. Note that ultrasound diagnostic apparatus 1 may generate arbitrary ultrasound images such as B-mode images, color Doppler images, three-dimensional ultrasound images, or M-mode images. Similarly, an arbitrary probe such as a convex probe, a linear probe, a sector probe, or a three-dimensional probe may be used as ultrasound probe 20.

Ultrasound probe 20 transmits ultrasound to the subject, receives an ultrasonic echo reflected by the subject, converts it to a reception signal, and transmits it to ultrasound diagnostic apparatus body 10. The details of ultrasound probe 20 will be described later.

Ultrasound diagnostic apparatus body 10 visualizes the internal state of the subject in an ultrasound image, using the reception signal from ultrasound probe 20. To be specific, ultrasound diagnostic apparatus body 10 includes operation input section 11, transmission section 12, reception section 13, image processing section 14, display section 15, and control section 16.

Operation input section 11 receives, for example, a command for instructing to start diagnosis or the like or an input of information on the subject. Operation input section 11 includes, for example, an operation panel having multiple input switches, a keyboard, and a mouse.

Transmission section 12 generates a transmission signal according to an instruction from control section 16 and transmits it to ultrasound probe 20.

Reception section 13 acquires the reception signal generated by ultrasound probe 20, performs reception processing (for example, phasing addition processing and filter processing) on the reception signal, and then outputs it to image processing section 14.

Image processing section 14 performs predetermined signal processing (for example, logarithmic compression processing, detection processing, or FFT analysis processing) on the reception signal acquired from reception section 13 in accordance with an instruction from control section 16, and generates ultrasound images showing the internal state (e.g., B-mode images, color Doppler images, or three-dimensional ultrasound images). Note that the content of the processing for generating ultrasound images is well known, and the description thereof will therefore be omitted here.

Display section 15, for example, a liquid crystal display, displays an ultrasound image generated in image processing section 14.

Control section 16 entirely controls ultrasound diagnostic apparatus 1 by controlling operation input section 11, transmission section 12, reception section 13, image processing section 14, and display section 15 according to their functions.

Schematic Configuration of Ultrasound Probe

Figure 3:
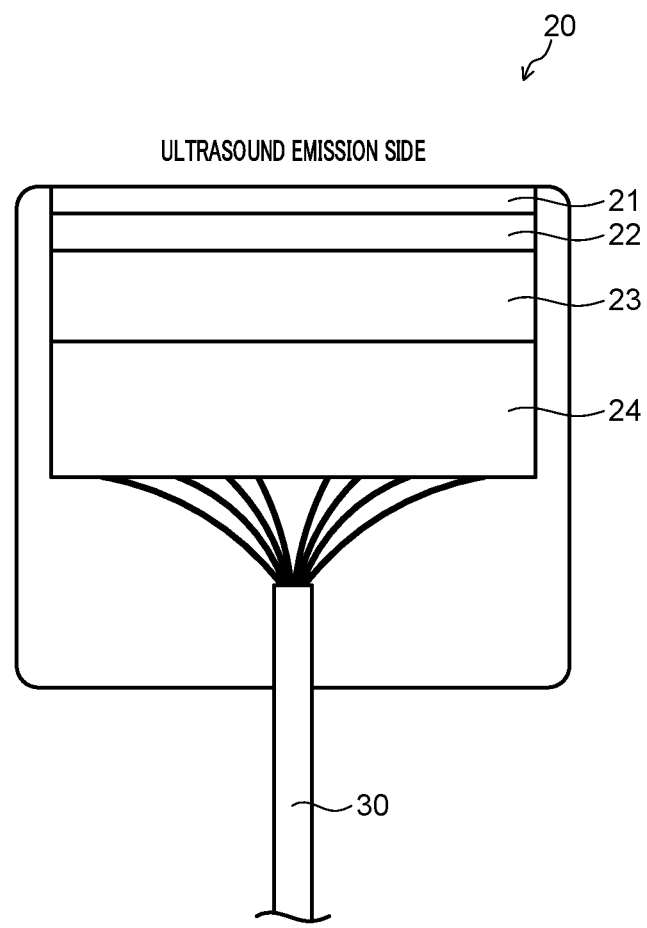
FIG. 3 is a diagram showing the configuration of the ultrasound probe according to Embodiment 1.

FIG. 3 is a diagram showing the configuration of ultrasound probe 20 according to this embodiment.

Ultrasound probe 20 includes protective layer 21, element array layer 22, circuit substrate 23, and backing member 24 in this order from the Ultrasound emission surface side.

Protective layer 21 protects the surface of element array layer 22 (that is, the Ultrasound emission surface). Protective layer 21 is composed of a material (for example, silicone rubber) that does not give discomfort when being brought into contact with a human body and has an acoustic impedance relatively close to that of the human body. Note that protective layer 21 may include an acoustic lens or matching layer.

Element array layer 22 is composed of multiple piezoelectric elements that are two-dimensionally arrayed in the ultrasound emission surface of ultrasound probe 20, transmits ultrasound toward the inside of the subject, and receives ultrasonic echoes reflected by the inside of the subject.

Circuit substrate 23 is a base on which element array layer 22 is formed. Circuit substrate 23 includes switching devices that drive and control the respective piezoelectric elements of element array layer 22, and a transmission circuit that generates a transmission signal for ultrasound transmission through the switching devices, and a reception circuit that detects the reception signal (ultrasound signal). Circuit substrate 23 is connected to ultrasound diagnostic apparatus body 10 (transmission section 12 and reception section 13) via cable 30.

Note that circuit substrate 23 may include a transmission/reception switching circuit and a beam former (phased addition circuit). In addition, signals between circuit substrate 23 and ultrasound diagnostic apparatus body 10 (transmission section 12 and reception section 13) may be transmitted and received by wireless communication instead of cable 30.

Backing member 24 attenuates the unnecessary vibration generated in element array layer 22.

Figure 4A:
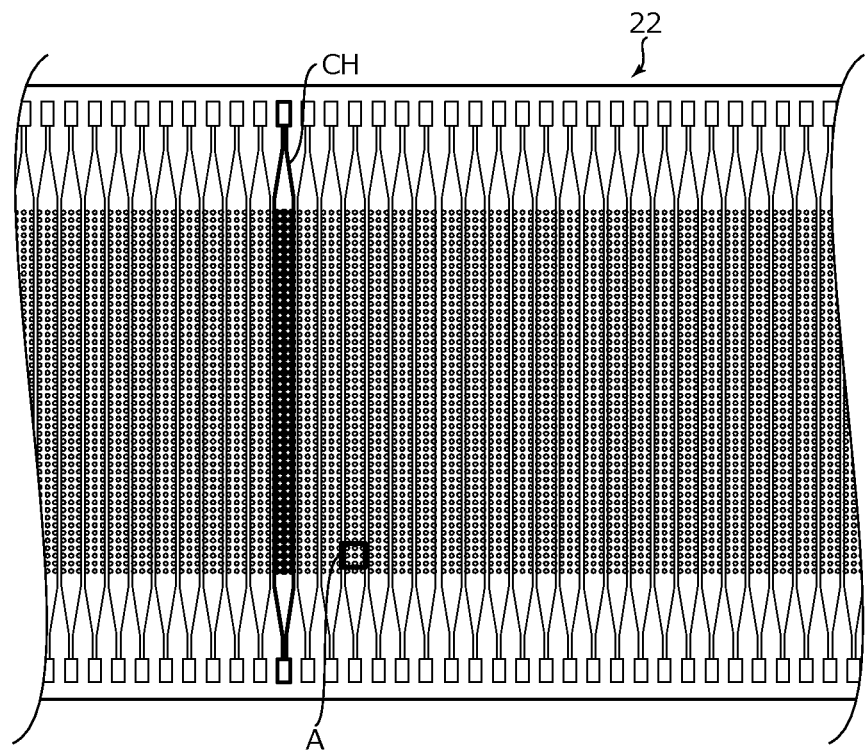
FIG. 4A is a plan view showing the configuration of an element array layer according to Embodiment 1.
Figure 4B:
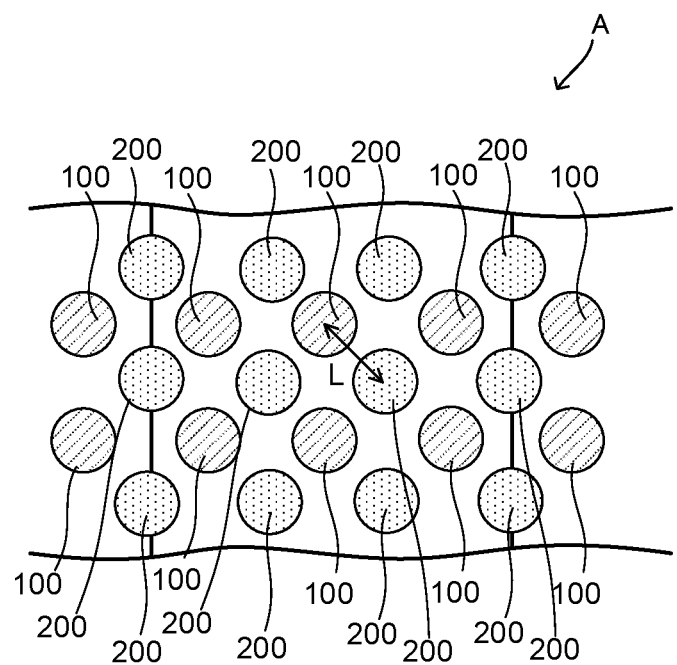
FIG. 4B is a plan view showing the configuration of the element array layer according to Embodiment 1.

FIGS. 4A and 4B are plan views showing the configuration of element array layer 22 according to this embodiment, from the upper surface side of element array layer 22, that is, the ultrasound emission surface side. FIG. 4B is an enlarged view of region A enclosed by the thick line in FIG. 4A.

Element array layer 22 includes first piezoelectric element 100 and second piezoelectric element 200 that are two-dimensionally arrayed in the ultrasound emission surface of ultrasound probe 20. First piezoelectric element 100 is a piezoelectric element for ultrasound transmission (hereinafter referred to as "transmission element 100"), and second piezoelectric element 200 is a piezoelectric element for ultrasound reception (hereinafter referred to as "reception element 200").

The ultrasound emission surface of ultrasound probe 20 is divided into multiple channels CH along the scanning direction, and multiple transmission elements 100 and reception elements 200 are provided in each channel CH. Transmission elements 100 and reception elements 200 are driven and controlled for each channel CH.

Transmission element 100 and reception element 200 each have, for example, a circular shape or a rectangular shape in a plan view (see FIG. 4B). For example, transmission element 100 and reception element 200 are alternately arranged in a checkered pattern in the ultrasonic emission surface in a plan view. Here, a "plan view" refers to a state in which ultrasound probe 20 is viewed from the ultrasonic emission surface side (the same applies hereinafter).

To be specific, transmission element 100 and reception element 200 are adjacent to each other so that their element regions do not overlap in the ultrasonic emission surface. The "element region" is an effective region where ultrasound is transmitted or received and, in a laminated structure including a piezoelectric body and two electrodes disposed on the upper surface side and the lower surface side of the piezoelectric body, is a region where all of the piezoelectric body and the two electrodes overlap each other (see FIG. 5).

In this embodiment, in order to increase the number of reception elements 200, reception elements 200 are also disposed at the boundaries of adjacent channels. Reception elements 200 disposed at the boundaries of adjacent channels are alternately allocated to any one channel during operation.

In element array layer 22, the element inter-center distance L between transmission element 100 and reception element 200 adjacent to each other is preferably $L \leq \lambda_c/2$ where the wavelength in the living body (representative sound speed 1530 m/sec) with respect to the center frequency $f_c$ of the band characteristic of ultrasound probe 20 is $\lambda_c$. Hence, transmission element 100 and reception element 200 can be regarded as the same sound source, and the paths of the transmission ultrasonic beam and the reception ultrasonic beam can be matched.

An aspect of the arrangement of transmission elements 100 and reception elements 200 is not limited to that shown in FIGS. 4A and 4B: for example, they may be arranged in a triangular lattice or grid or in a random fashion. The arrangement and shape of transmission elements 100 or reception elements 200 may be different between on the outer side and the inner side with respect to the short axis direction of ultrasound probe 20.

The number of transmission elements 100 and reception elements 200 in each channel CH may be the same or different. For example, in the case where the transmission sound pressure intensity can be secured with a small number of cells, it is desirable to reduce the number of transmission elements 100 and increase the number of reception elements 200 in each channel CH.

Detailed Configuration of Ultrasound Probe

Figure 5:
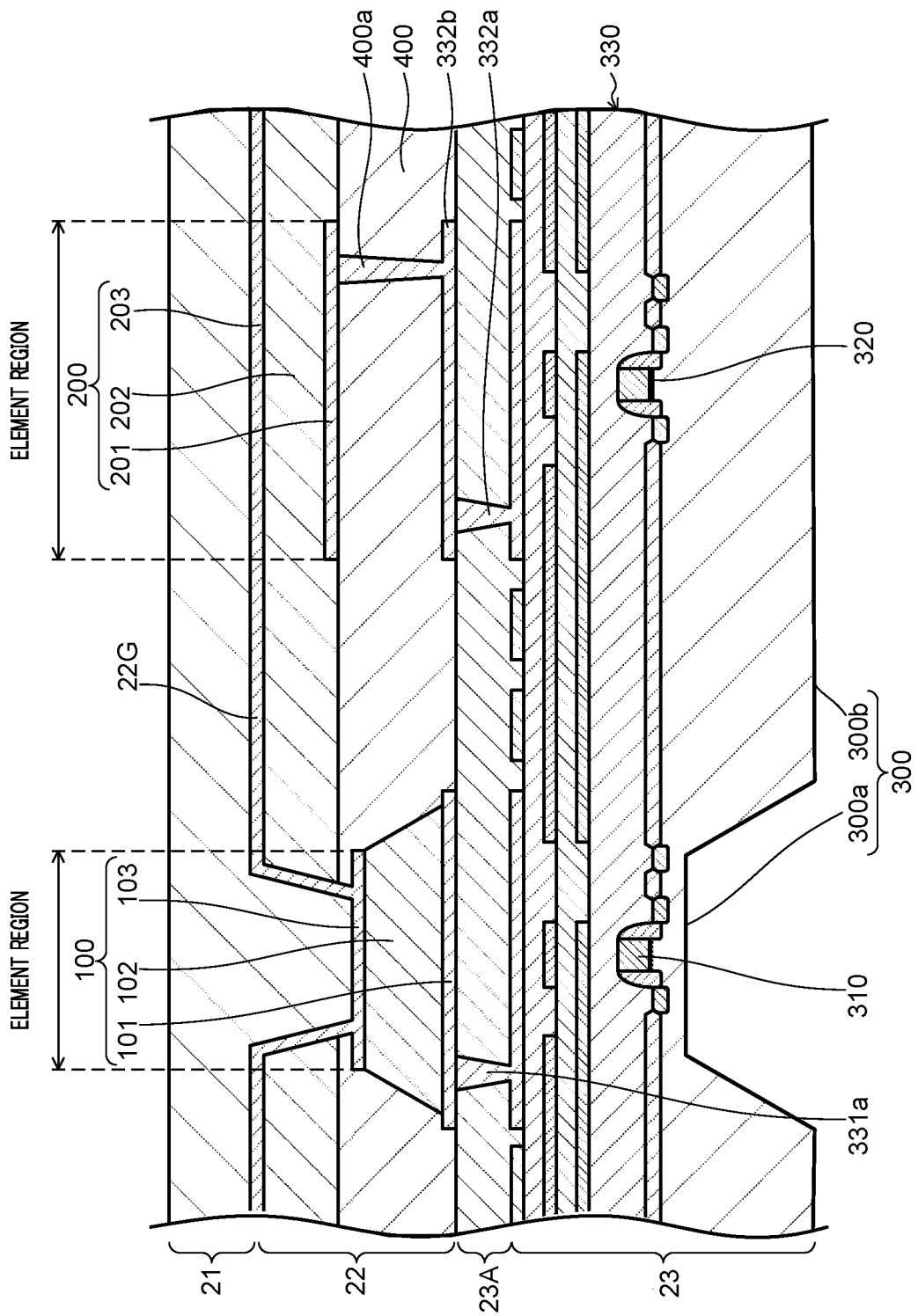
FIG. 5 is a sectional view showing the configuration of an ultrasound probe according to Embodiment 1.

FIG. 5 is a sectional view showing a configuration of ultrasound probe 20 according to this embodiment. Note that illustration of backing member 24 is omitted in FIG. 5. The ultrasonic emission surface side of ultrasound probe 20 will be hereinafter referred to as "upper side", and the opposite side to the ultrasonic emission surface will be referred to as "lower side".

Ultrasound probe 20 has a structure in which insulating layer 23A, element array layer 22, and protective layer 21 are laminated on circuit substrate 23 in this order from the lower side. Buffer layer 400 is present between reception element 200 in element array layer 22 and insulating layer 23A.

Circuit substrate 23 is, for example, a substrate for circuitry on which transmission transistor 310, reception transistor 320, and wiring layer 330 are formed on substrate 300 (for example, a Si substrate).

Transmission transistor 310 generates a transmission signal and controls the operation of transmission element 100. Reception transistor 320 amplifies the reception signal generated by reception element 200. On circuit substrate 23, different CMOS circuits are made up of respective transmission transistors 310 corresponding to the respective transmission elements 100, and different CMOS circuits are made up of reception transistors 320 corresponding to respective reception elements 200.

Wiring layer 330 includes a wiring section that electrically connects transmission transistor 310 and transmission element 100 with each other, and a wiring section that electrically connects reception transistor 320 and reception element 200 with each other.

Substrate 300 has thin film section 300a, in a plan view, in a portion corresponding to a region of the bottom surface of that substrate 300 (that is, the opposite side to the side on which transmission element 100 is formed; the same applies hereinafter) where each transmission element 100 is formed (that is, the element region). Thin film section 300a is formed by etching a portion of the lower surface of substrate 300 corresponding to the region where transmission element 100 is formed, into a concave shape. In other words, thin film section 300a is formed on the lower surface of substrate 300 in a position overlapping the region where each transmission element 100 is formed. Substrate 300 constitutes a diaphragm structure below the region where transmission element 100 is formed.

Meanwhile, a portion of the lower surface of substrate 300 corresponding to the region where each reception element 200 of substrate 300 is formed (that is, the element region) is not etched and is thicker than thin film section 300a (hereinafter also referred to as "thick film section 300b"). In other words, substrate 300 forms a non-diaphragm structure below the region where reception element 200 is formed (corresponding to the "second region" of the present invention).

Here, the upper surface of circuit substrate 23 is the surface on the upper side in FIG. 5 and refers to the surface on the ultrasound transmission/reception surface side of ultrasound probe 20 (the same applies hereinafter). The lower surface of circuit substrate 23 is the surface on the lower side in FIG. 5 and refers to the surface opposite to the ultrasound transmission/reception surface of ultrasound probe 20 (the same applies hereinafter).

For convenience of explanation, wiring layer 330 is shown with a thickness equivalent to that of substrate 300 in the drawing. In reality, wiring layer 330 is extremely thinner than substrate 300. Accordingly, the thickness of circuit substrate 23 substantially corresponds to the thickness of substrate 300.

Insulating layer 23A is a protective layer for circuit substrate 23 formed so as to cover the entire upper surface of circuit substrate 23. Insulating layer 23A insulates heat to prevent circuit substrate 23 from being deteriorated by being heated when the piezoelectric film of element array layer 22 is formed.

In insulating layer 23A, through electrode 331a that electrically connects the wiring section of wiring layer 330 connected to transmission transistor 310 with transmission element 100, and through electrode 332a that electrically connects the wiring section of wiring layer 330 connected to reception transistor 320 with reception element 200 are formed. On insulating layer 23A, wiring section 332b that connects through electrode 332a and through electrode 400a provided in buffer layer 400 is formed.

Insulating layer 23A is composed of, for example, $SiO_2$ or porous silicon. Insulating layer 23A may have a single layer structure or a multilayer structure. The thickness of insulating layer 23A is, for example, 3 µm or more.

Transmission element 100 includes first lower electrode 101, first piezoelectric body 102, and first upper electrode 103, which are laminated on insulating layer 23A in this order from the lower side. Transmission element 100 has a unimorph structure in which first piezoelectric body 102 is sandwiched between first lower electrode 101 and first upper electrode 103. Note that buffer layer 400 is not present between transmission element 100 and insulating layer 23A.

First lower electrode 101 is electrically connected to transmission transistor 310 via through electrode 331a provided in insulating layer 23A and wiring layer 330 of the circuit substrate. First upper electrode 103 is connected to GND via common electrode 22G routed around the upper surface of element array layer 22.

First lower electrode 101 and first upper electrode 103 are composed of, for example, a metal material such as Pt, Au, or Ti, or a conductive oxide. Note that first lower electrode 101 and first upper electrode 103 may be a laminate of multiple different metal materials or a laminate of a metal material and a conductive oxide.

First piezoelectric body 102 is typically composed of an inorganic piezoelectric material having excellent ultrasound transmission performance (that is, transmission sensitivity and available frequency band). First piezoelectric body 102 is preferably composed of a material having a large inverse piezoelectric constant, for example, lead zirconate titanate (PZT).

Transmission element 100 is formed on thin film section 300a of substrate 300 constituting the diaphragm structure. Consequently, upon voltage application, transmission element 100 vibrates in the flexural vibration mode on circuit substrate 23 and emits ultrasound.

Here, a diaphragm structure refers to a structure that induces the bending mode resonance of the diaphragm held at an end in a frequency band (−40 dB bandwidth) in which ultrasound is transmitted. The bending of the diaphragm refers to the displacement of the diaphragm in the vertical direction (thickness direction) caused when the piezoelectric body (here, transmission element 100) extends and contracts in the direction in which the plate surface of the diaphragm (here, thin film section 300a) extends (that is, the direction orthogonal to the thickness direction of circuit substrate 23).

Transmission element 100 preferably has one or more resonance points in the frequency band used for transmitting ultrasound. Hence, high transmission sensitivity can be obtained in the vicinity of the resonance point. The transmission sensitivity characteristic is the ultrasound intensity (sound pressure intensity) and is proportional to the product of the transducer displacement and the frequency, and thus does not abruptly attenuate even at frequencies higher than the resonance frequency, so that the bandwidth can be made wider even with a resonance point. Since transmission element 100 vibrates in the flexural vibration mode on circuit substrate 23, the resonance point of that transmission element 100 also depends on the diaphragm structure of substrate 300.

It is preferable that transmission element 100 be designed such that the effective acoustic impedance matches the acoustic impedance of the living body. Hence, ultrasound can be efficiently propagated in the living body. To be specific, the rigidity of the diaphragm structure of substrate 300 is preferably optimized. Depending on the required resonance frequency, transmission performance (transmission sensitivity or frequency band), and the like, the material of substrate 300, the thickness of thin film section 300a, the thickness of first piezoelectric body 102, the element region of transmission element 100, and the like are optimized as appropriate.

Reception element 200 is formed on insulating layer 23A with buffer layer 400 is located therebetween. Reception element 200 includes second lower electrode 201, second piezoelectric body 202, and second upper electrode 203, which are layered in this order on buffer layer 400 from the lower side. Reception element 200 has a unimorph structure in which second piezoelectric body 202 is sandwiched between second lower electrode 201 and second upper electrode 203.

Second lower electrode 201 is electrically connected to reception transistor 320 through electrode 400a provided in buffer layer 400, wiring section 332b provided on insulating layer 23A, through electrode 332a provided in insulating layer 23A, and wiring layer 330 of circuit substrate 23.

Second upper electrode 203 is connected to GND via common electrode 22G routed on the upper surface of element array layer 22. In this embodiment, second upper electrode 203 is configured as a part of common electrode 22G.

Second lower electrode 201 and second upper electrode 203 are composed of, for example, a metal material such as Pt, Au, or Ti, or a conductive oxide. Note that second lower electrode 201 and second upper electrode 203 may be a laminate of multiple different metal materials or a laminate of a metal material and a conductive oxide.

Second piezoelectric body 202 generates voltage by receiving ultrasound. Second piezoelectric body 202 is preferably composed of an organic piezoelectric material having excellent ultrasound reception performance (that is, reception sensitivity and available frequency band), for example, polyvinylidene fluoride (PVDF) resin (a copolymer based on PVDF resin). PVDF is inferior in ultrasound transmission performance to PZT, but has low dielectric constant and thus very high voltage reception performance. For example, a piezoelectric element with PVDF has a voltage reception sensitivity about 10 times that of a piezoelectric element with PZT.

Reception element 200 is formed on thick film section 300b of substrate 300 of the non-diaphragm structure. Consequently, upon reception of ultrasound, reception element 200 deforms in the thickness direction and generates voltage. In other words, reception element 200 vibrates in the thickness vibration mode on circuit substrate 23.

It is preferable that reception element 200 does not have a resonance point in the frequency band. Hence, a wide reception bandwidth can be obtained. This is because the reception sensitivity is equivalent to a voltage signal, is proportional to the displacement of the transducer, and sharply attenuates on the high frequency side from the resonance frequency and becomes a narrow band when a resonance point is in the frequency band. From this point of view, in order to drive reception element 200 in a frequency band lower than or equal to the resonance point, the total thickness of reception element 200 (second piezoelectric body 202) and buffer layer 400 is ¼ or less of the wavelength of the ultrasound (the details will be described later).

Buffer layer 400 is formed on insulating layer 23A and directly below the region where reception element 200 is formed so as to be present between insulating layer 23A and reception element 200. Buffer layer 400 reduces the degradation of the reception signal due to the parasitic capacitance of reception transistor 32 (hereinafter also referred to as "transistor parasitic capacitance"), and can function as a backing member that suppresses the reverberation of the ultrasound that travels from element array layer 22 toward circuit substrate 23. The effect of buffer layer 400 in reducing the transistor parasitic capacitance will be described later with reference to FIGS. 6A and 6B.

However, buffer layer 400 may hinder the flexural vibration of transmission element 100 and degrade the transmission characteristics of transmission element 100. For this reason, in ultrasound probe 20 according to this embodiment, buffer layer 400 is not provided in a region directly below transmission element 100.

Buffer layer 400 is preferably an insulating material having a relative dielectric constant of 4 or less in order to reduce transistor parasitic capacitance, and is composed of, for example, silicon oxide, parylene, polyimide, polyethylene, or silicone rubber. In this embodiment, polyimide is used as buffer layer 400.

However, in order for the function as the backing member to be effectively exhibited, it is preferable to use an organic insulating material such as parylene, polyimide, polyethylene, or silicone rubber for buffer layer 400. In particular, buffer layer 400 is preferably composed of a material that satisfies the condition expressed by the following formula (1) or the following formula (2). When an anisotropic material is used for buffer layer 400, the elastic modulus in the following formula (2) is a larger one of the tensile and compressive elastic modulus of the transmission piezoelectric material in the elongation direction (the in-plane direction vertical to the normal slope).

$$g2/g1<10 \qquad \text{Formula (1)}$$

where g1 is the elastic modulus of second piezoelectric body 202, and g2 is the elastic modulus of buffer layer 400.

$$Z2/Z1<1 \qquad \text{Formula (2)}$$

where Z1 is the acoustic impedance of second piezoelectric body 202, and Z2 is the acoustic impedance of buffer layer 400.

Buffer layer 400 is formed using, for example, a printing method. FIG. 5 shows a mode in which buffer layer 400 is formed by a printing method. Buffer layer 400 surrounds, for example, the periphery of transmission element 100, and is formed such that the position of the upper end of that buffer layer 400 is higher than the position of the upper end of transmission element 100.

With the position of the upper end of buffer layer 400 made higher than the position of the upper end of transmission element 100 in this manner, when buffer layer 400 is formed on insulating layer 23A, it can be formed in the entire region of insulating layer 23A so as to cover transmission element 100 (which will be described later with reference to FIG. 7C). This makes the surface of buffer layer 400 smooth, and enables formation of a uniform film when second piezoelectric body 202 of reception element 200 is formed thereafter by application.

If a material having a low elastic modulus is used as buffer layer 400, the phenomenon in which buffer layer 400 hinders operation of transmission element 100 can be eased even when buffer layer 400 is in contact with the side of transmission element 100. Buffer layer 400 is preferably composed of a material having an elastic modulus of ¹⁄₁₀ or less of the elastic modulus of the piezoelectric material of transmission element 100, and an organic material that does not contain a filler can be used as a material that satisfies this condition.

Next, the effect of buffer layer 400 in reducing the transistor parasitic capacitance will be described with reference to FIGS. 6A and 6B.

Figure 6A:
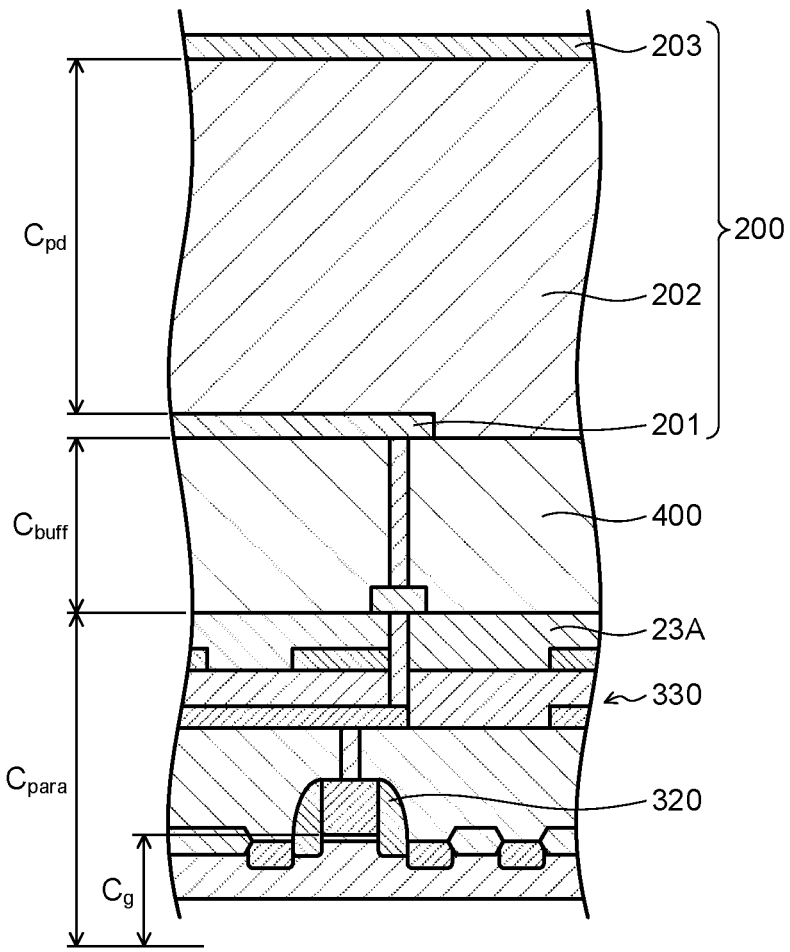
FIG. 6A is a diagram showing parasitic capacitance existing between a reception element and a substrate.
Figure 6B:
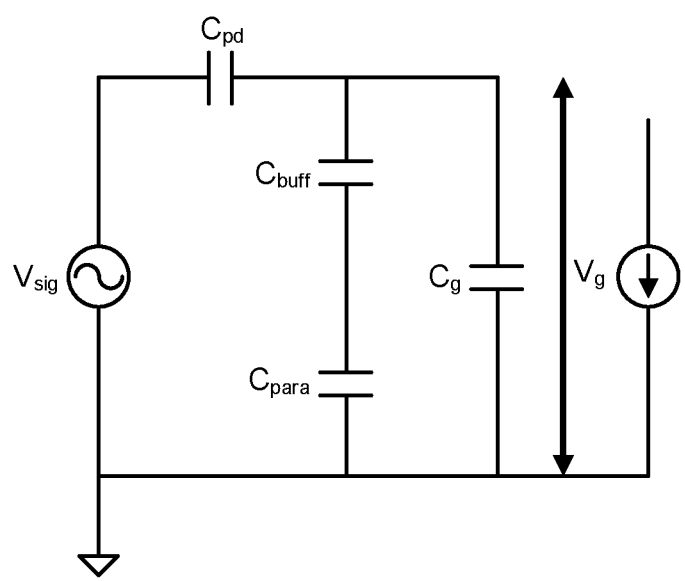
FIG. 6B is a diagram showing the equivalent circuit of a reception circuit for detecting a reception signal generated by reception element.

FIG. 6A is a diagram showing parasitic capacitance existing between reception element 200 and substrate 300, and FIG. 6B is a diagram showing a circuit equivalent to a reception circuit that detects a reception signal generated by reception element 200.

In FIGS. 6A and 6B, $V_{sig}$ is the signal source (that is, reception element 200), $C_{pd}$ is the capacitance of reception element 200, $C_{bar}$ is the capacitance of buffer layer 400, $C_{para}$ is the parasitic capacitance of reception transistor 320, $C_g$ is the input capacitance (that is, the gate capacitance) of reception transistor 320, and $V_g$ is the gate input voltage to reception transistor 320.

In general, in order to improve the reception performance of ultrasound probe 20, it is important to maximize the input signal (that is, the gate input voltage) to reception transistor 320 when reception element 200 generates a reception signal.

In addition, from the viewpoint of impedance matching of the signal path from reception element 200 to reception transistor 320, reception transistor 320 and reception element 200 are preferably set so that input capacitance $C_g$ of reception transistor 320 and electrostatic capacitance $C_{pd}$ of reception element 200 match.

From this point of view, when reception transistor 320 side is viewed from signal source $V_{sig}$ side, the parasitic capacitance $C_{para}$ of that reception transistor 320 is required to be equivalently close to zero.

Note that parasitic capacitance $C_{para}$ of reception transistor 320 is, for example, gate-source capacitance, gate-drain capacitance, and the like that appear in parallel with input capacitance $C_g$ of reception transistor 320 formed between the gate (here, the input electrode) and substrate 300.

Parasitic capacitance $C_{para}$ of reception transistor 320 is a factor that causes signal degradation of the reception signal generated by reception element 200.

In this regard, as shown in FIG. 6B, the capacitance provided by buffer layer 400 is equivalent to electrostatic capacitance $C_{buff}$ connected in series with parasitic capacitance $C_{para}$ of reception transistor 320 when reception transistor 320 side is viewed from signal source $V_{sig}$. In other words, combined capacitance $C_{all}$ can be expressed by Formula (3) below when reception transistor 320 side is viewed from signal source $V_{sig}$.

$$C_{all}=C_g+(C_{para}\times C_{buff})/(C_{para}+C_{buff}) \quad \text{Formula (3)}$$

Here, reducing electrostatic capacitance $C_{buff}$ of buffer layer 400 can bring the series-combined capacitance of electrostatic capacitance $C_{buff}$ of buffer layer 400 and parasitic capacitance $C_{para}$ of reception transistor 320 (the second term of Formula (3)) close to zero. At this time, combined capacity $C_{all}$ obtained when reception transistor 320 side is viewed from signal source $V_{sig}$ is equivalent to only input capacitance $C_g$ of reception transistor 320 formed between the gate of reception transistor 320 and substrate 300.

As described above, buffer layer 400 provided between reception element 200 and insulating layer 23A can increase the sensitivity of reception transistor 320. In other words, this makes it possible to increase the gate input signal in reception transistor 320.

How the thickness of buffer layer 400 is to be set will now be described.

Since buffer layer 400 is composed of a material having a low elastic modulus (for example, polyimide) like second piezoelectric body (for example, PVDF) 202, that buffer layer 400 vibrates together and integrally with reception element 200. Therefore, the frequency at which reception element 200 resonates is determined by the total thickness of second piezoelectric body 202 and buffer layer 400. At this time, insulating layer 23A can be regarded as a fixed end during vibration along the thickness of reception element 200 and buffer layer 400.

Accordingly, in order to drive reception element 200 in the frequency band lower than or equal to the resonance point, the sum of the thickness of second piezoelectric body 202 and the thickness of buffer layer 400 needs to be ¼ or less of the wavelength of the ultrasound used for transmission and reception, as shown in Formula (4) below.

$$t \le v/4\ f_{max} \quad \text{Formula (4)}$$

Here, in Formula (4), t is the sum of the thickness of reception element 200 and the thickness of buffer layer 400; v is the average of the sound speed in reception element 200 (that is, second piezoelectric body 202) and the sound speed in buffer layer 400; and $f_{max}$ is the maximum frequency in the frequency band used for transmission/reception of ultrasound, and represents, for example, the frequency twice the center frequency (transmission frequency) of the frequency band characteristic of ultrasound probe 20.

Hence, in reception element 200, resonance in the thickness direction can be prevented and a wide bandwidth can be ensured.

Here, it is preferable that the thickness of buffer layer 400 be increased in order to reduce the capacitance of that buffer layer 400. On the other hand, increasing the thickness of buffer layer 400 decreases the maximum frequency that can be used for transmission and reception of ultrasound. On the other hand, increasing the thickness of buffer layer 400 under the condition expressed by Formula (4) reduces the thickness of second piezoelectric body 202 of reception element 200, and reduces the reception sensitivity of reception element 200. For this reason, the thickness of buffer layer 400 is preferably set as appropriate in consideration of, in addition to the capacitance of that buffer layer 400, the maximum frequency used for transmission/reception of ultrasound and the reception sensitivity of reception element 200.

Table 1 below shows an example of gate input voltage $V_g$, the amplification sensitivity by buffer layer 400, and maximum frequency $f_{max}$ obtained when the material and thickness of buffer layer 400 are changed. Maximum frequency $f_{max}$ is calculated by $f_{max}=v/4t$ as in Formula (4) above. Here, PVDF is used as second piezoelectric body 202 of reception element 200.

TABLE 1

| Material of buffer layer | Buffer layer thickness (μm) | Gate input voltage Vg (V) | Amplification sensitivity (reference is gate input voltage Vg without buffer layer) | Maximum frequency fmax (MHz) |
|---|---|---|---|---|
| Without buffer layer (second piezoelectric body PVDF thickness of 32 μm) | 0 | 0.7 | 1 | 20 |
| TEOS-SiO2 (second piezoelectric body PVDF thickness of 32 μm) | 2 | 1 | 1.5 | 20 |
| | 5 | 1.3 | 1.9 | 20 |
| | 10 | 1.6 | 2.2 | 20 |
| | 20 | 1.8 | 2.5 | 20 |
| | 30 | 1.9 | 2.7 | 20 |
| Polyimide (second piezoelectric body PVDF thickness of 32 μm) | 2 | 1.1 | 1.6 | 18.7 |
| | 5 | 1.4 | 2 | 17.1 |
| | 10 | 1.7 | 2.4 | 14.9 |
| | 20 | 1.8 | 2.6 | 11.8 |
| | 30 | 1.9 | 2.7 | 9.8 |
| Polyimide (second piezoelectric body PVDF thickness of 16 μm) | 2 | 0.9 | 1.4 | 35.2 |
| | 5 | 1.2 | 1.7 | 29.8 |
| | 10 | 1.3 | 1.9 | 23.7 |
| | 20 | 1.4 | 2 | 16.8 |
| | 30 | 1.5 | 2.1 | 13 |

In general, a frequency band of about 10 MHz is required as the maximum frequency of ultrasound used in medical ultrasound diagnostic apparatus 1. In this regard, Table 1 shows that, regardless of whether an inorganic material or an organic material is used as buffer layer 400, the maximum frequency of ultrasound of about 10 MHz can be ensured when the thickness of buffer layer 400 is 30 μm or less.

Meanwhile, Table 1 shows that, regardless of whether an inorganic material or an organic material is used as buffer layer 400, the amplification effect of the gate input voltage can be obtained when the thickness of buffer layer 400 is 2 μm or more.

From such a viewpoint, it is preferable that the thickness of buffer layer 400 be 2 μm to 30 μm. However, the thickness of that buffer layer 400 may be changed as appropriate from the above range according to the material of second piezoelectric body 202 of reception element 200, the maximum frequency of the required ultrasound, and the like. When the thickness of buffer layer 400 is less than 2 μm, the effect of reducing the parasitic capacitance disappears, and when the thickness of buffer layer 400 is greater than 30 μm, the band is narrowed because the resonance frequency is lowered.

Process of Manufacturing Ultrasound Probe

Next, a process of manufacturing ultrasound probe 20 according to this embodiment will be described with reference to FIGS. 7A to 7F.

FIGS. 7A to 7F are diagrams showing the process of manufacturing ultrasound probe 20 according to this embodiment in time series.

Figure 7A:
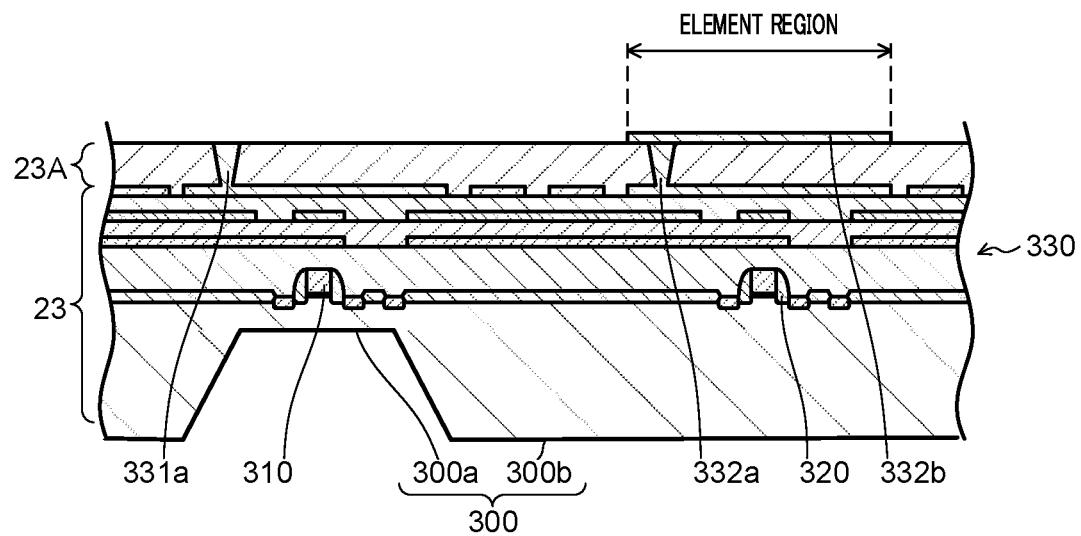
FIG. 7A is a diagram showing, in time series, the process for manufacturing the ultrasound probe according to Embodiment 1.

FIG. 7A shows the step of preparing circuit substrate 23. In this step, a reception circuit, such as reception transistor 320, and a transmission circuit, such as transmission transistor 310, are formed on substrate 300, and wiring layer 330 and insulating layer 23A are then formed on the reception circuit and the transmission circuit. After insulating layer 23A is formed, through electrodes 331a and 332a are formed in insulating layer 23A, and wiring section 332b is formed on insulating layer 23A. In this step, recess 300a is formed in the portion corresponding to the region where transmission element 100 is to be formed on the lower surface of substrate 300.

Figure 7B:
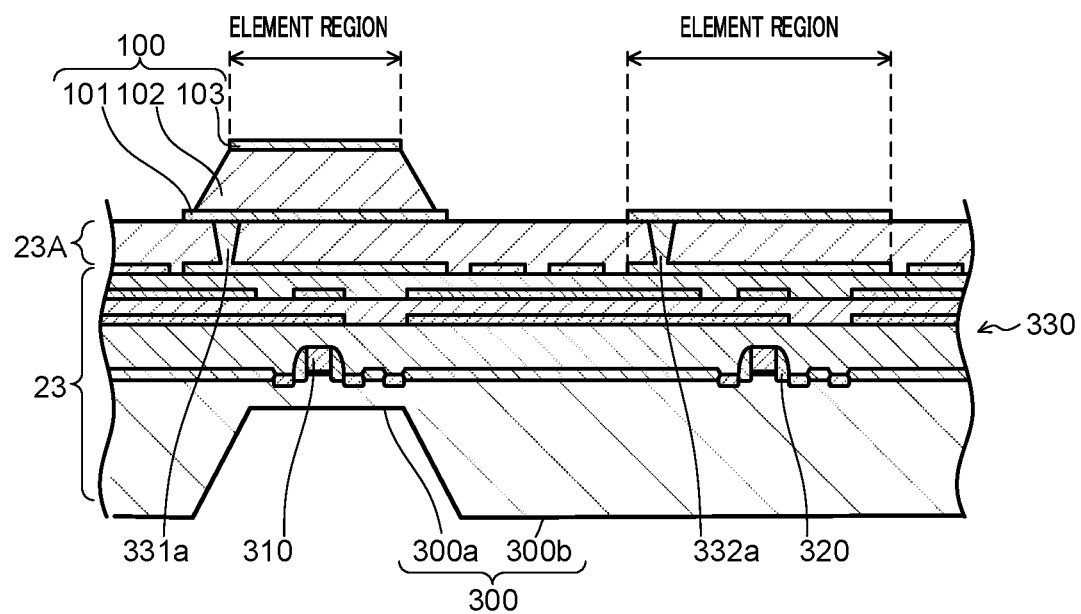
FIG. 7B is a diagram showing, in time series, the process for manufacturing the ultrasound probe according to Embodiment 1.

FIG. 7B shows the step of forming transmission element 100. In this step, materials for forming first lower electrode 101, first piezoelectric body 102, and first upper electrode 103 are sequentially formed on insulating layer 23A. Subsequently, the resist patterns provided on the upper part of the region where transmission element 100 is to be formed are etched to pattern first lower electrode 101, first piezoelectric body 102, and first upper electrode 103, thereby forming transmission element 100.

Figure 7C:
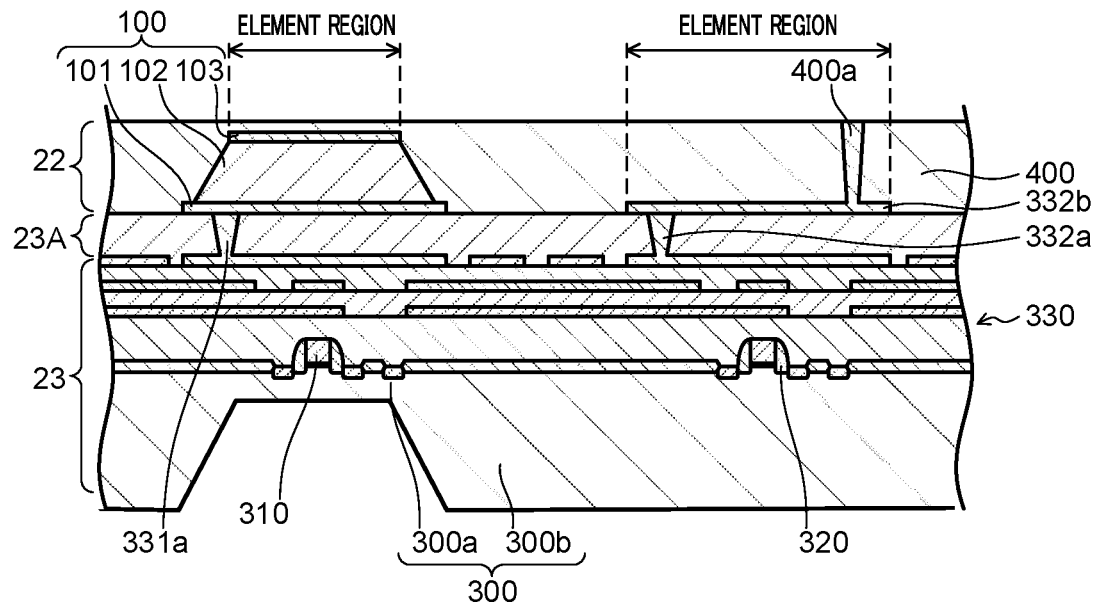
FIG. 7C is a diagram showing, in time series, the process for manufacturing the ultrasound probe according to Embodiment 1.

FIG. 7C shows the step of forming buffer layer 400. In this step, for example, buffer layer 400 is formed on insulating layer 23A and up to a position higher than the upper end of transmission element 100 by a printing method. Subsequently, through electrode 400a is formed in buffer layer 400.

Figure 7D:
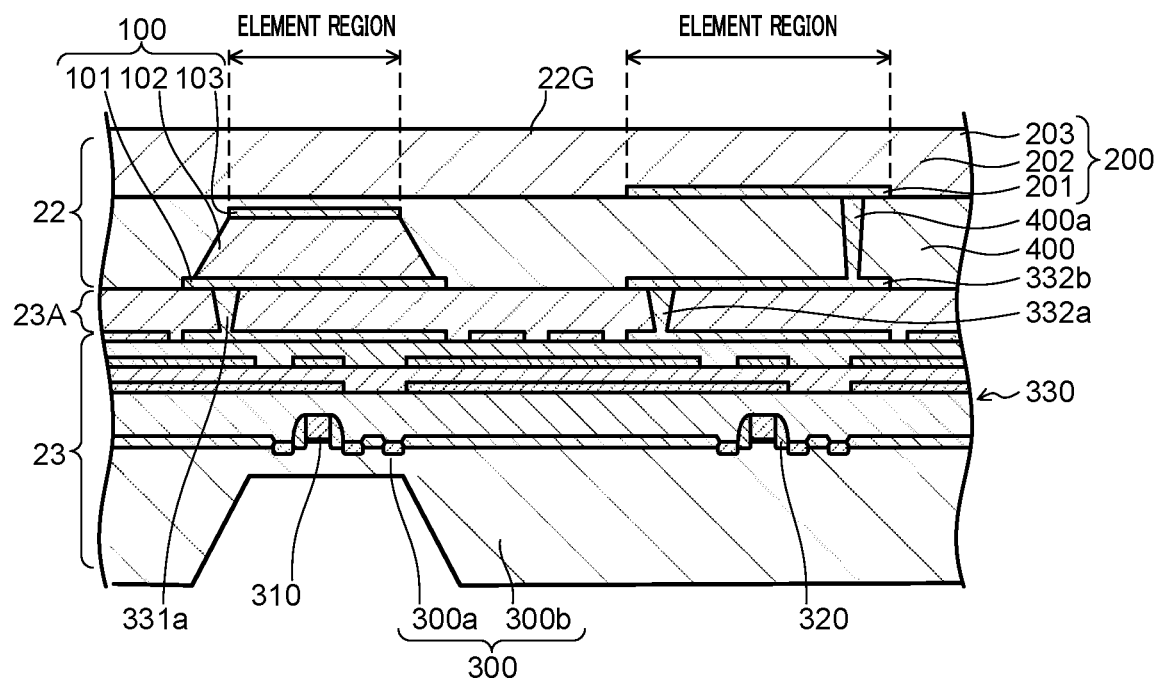
FIG. 7D is a diagram showing, in time series, the process for manufacturing the ultrasound probe according to Embodiment 1.

FIG. 7D shows the step of forming reception element 200. In this step, a pattern of second lower electrode 201 is first formed on buffer layer 400. Afterwards, a material (here, PVDF) for forming second piezoelectric body 202 is formed on the entire surface of buffer layer 400 by, for example, a printing method.

Figure 7E:
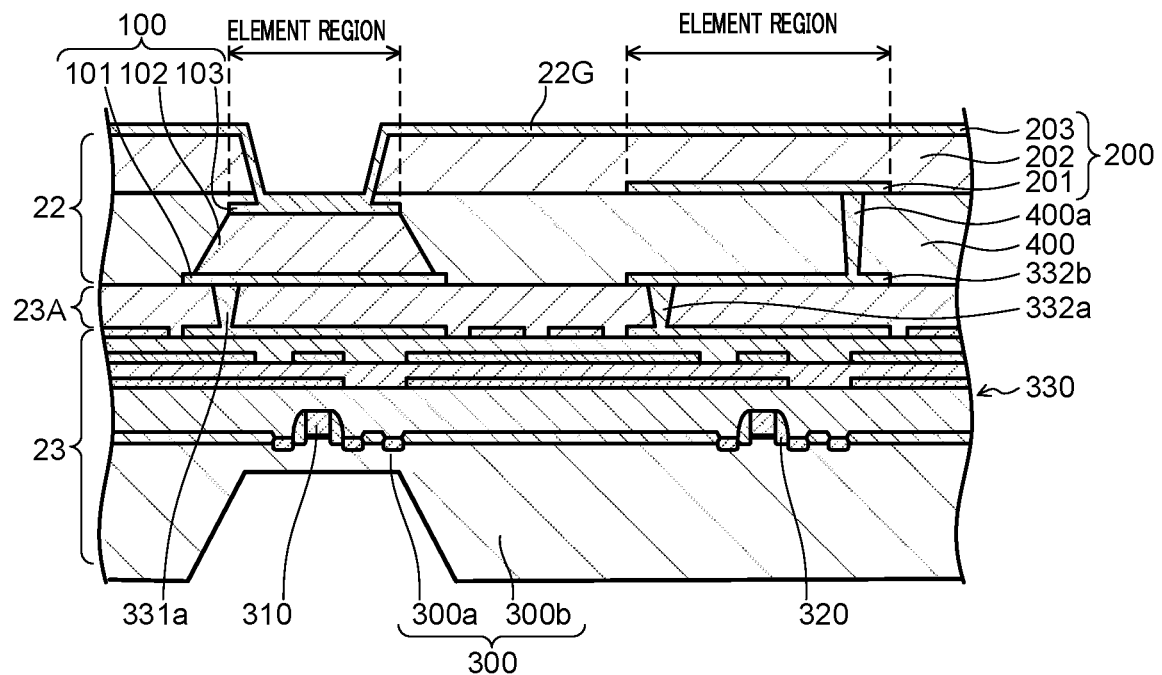
FIG. 7E is a diagram showing, in time series, the process for manufacturing the ultrasound probe according to Embodiment 1.

FIG. 7E shows the step of forming common electrode 22G. In this step, an opening communicating with first upper electrode 103 of transmission element 100 is formed in the piezoelectric material for second piezoelectric body 202 and buffer layer 400 by etching (for example, dry etching using $O_2$ plasma). Subsequently, common electrode 22G is formed entirely on second piezoelectric body 202 and first upper electrode 103 of transmission element 100. Consequently, a part of common electrode 22G becomes second upper electrode 203 and reception element 200 is formed.

Figure 7F:
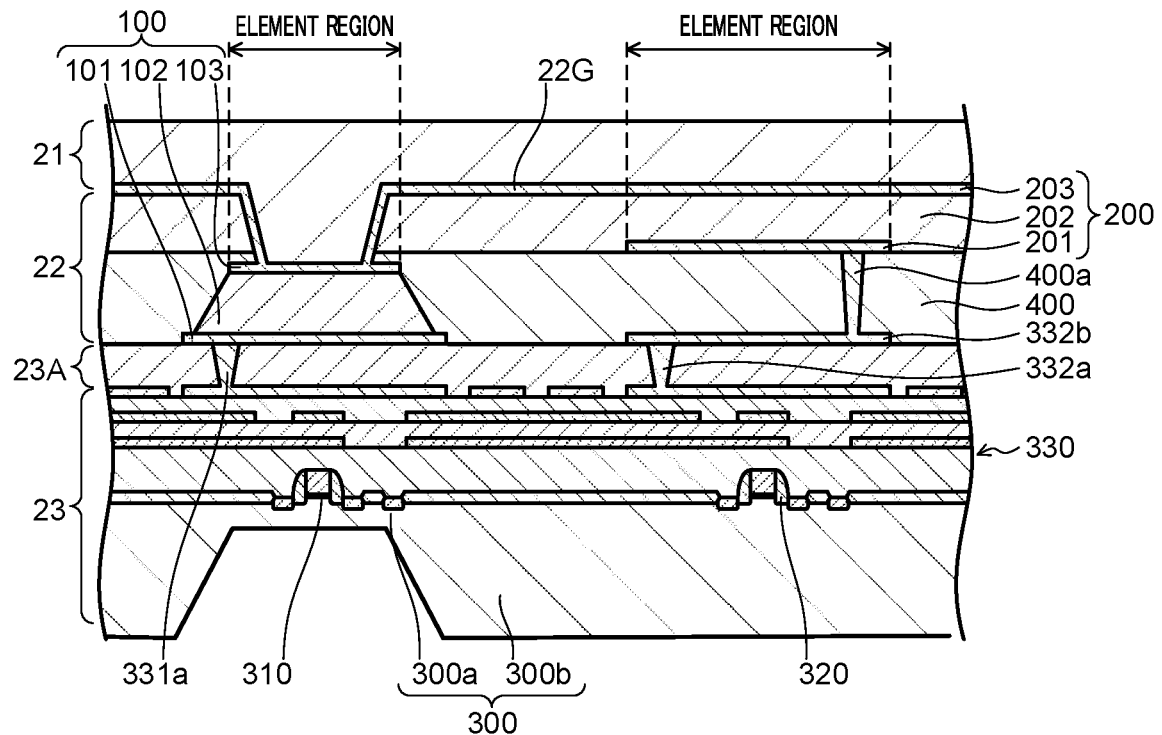
FIG. 7F is a diagram showing, in time series, the process for manufacturing the ultrasound probe according to Embodiment 1.

FIG. 7F shows the step of forming protective layer 21. In this step, protective layer 21 is formed so as to cover the entire transmission element 100 and reception element 200.

As described above, with the configuration of ultrasound probe 20 according to this embodiment, ultrasound probe 20 having high transmission/reception sensitivity over a wide frequency band can be manufactured with a simple manufacturing process.

Advantageous Effects

As described above, in ultrasound probe 20 according to this embodiment, transmission element 100 is configured to vibrate in the flexural vibration mode, and reception element 200 is configured to vibrate in the thickness vibration mode. Hence, high transmission/reception sensitivity can be attained over a wide frequency band. With this configuration, since it is not necessary to form a recess (thin film section 300a) on substrate 300 in the region where reception element 200 is formed, there is the advantage that transmission element 100 can be formed in high density.

In particular, with ultrasound probe 20 according to this embodiment, buffer layer 400 provided in the region immediately below reception element 200 can substantially increase the reception sensitivity of reception element 200 without causing the transmission characteristics of transmission element 100 to deteriorate.

In addition, with ultrasound probe 20 according to this embodiment, buffer layer 400 also functions as a backing member, so that deterioration in the reception performance of reception element 200 due to reflection by circuit substrate 23 can be suppressed. This can also reduce crosstalk between the two transmission elements 100 adjacent to each other.

Embodiment 2

Figure 8:
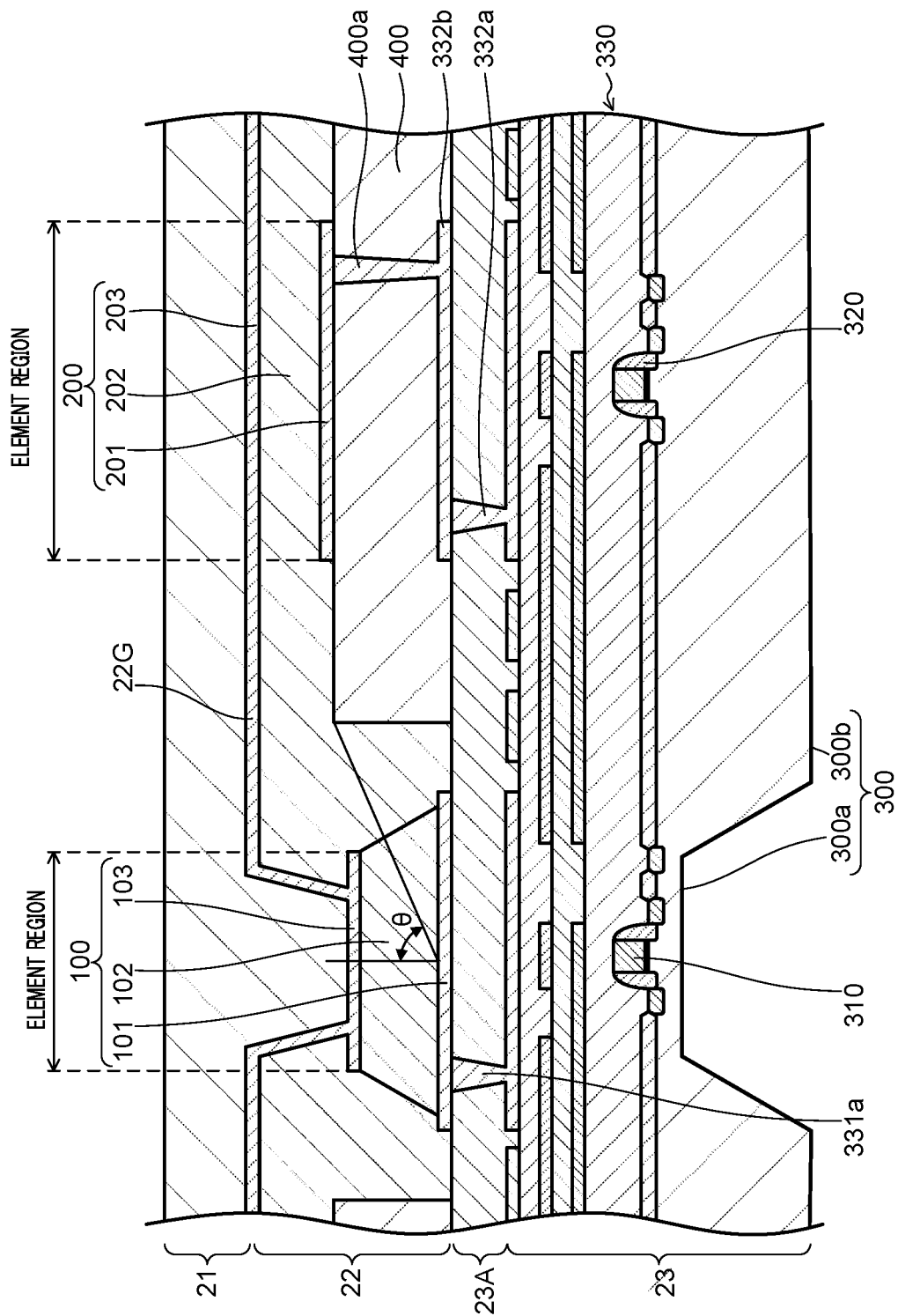
FIG. 8 is a sectional view showing the configuration of an ultrasound probe according to Embodiment 2.

The configuration of ultrasound probe 20 according to Embodiment 2 will be described with reference to FIG. 8. FIG. 8 is a sectional view showing the configuration of ultrasound probe 20 according to Embodiment 2.

Ultrasound probe 20 according to this embodiment is different from Embodiment 1 in that buffer layer 400 is not in contact with transmission element 100. Description of the configuration shared with Embodiment 1 will be omitted (the same applies to the other embodiments).

As described above, a material having a low elastic modulus (typically, an organic insulating material) is used as buffer layer 400. Consequently, even if that buffer layer 400 is in contact with transmission element 100, the degree of inhibition of operation of transmission element 100 by that buffer layer 400 is small. However, when an inorganic material (for example, silicon oxide) having an elastic modulus larger than $1/10$ of the piezoelectric material is used as buffer layer 400, that buffer layer 400 may hinder operation of transmission element 100. In addition, buffer layer 400 may hinder the travel of the ultrasound beam emitted from transmission element 100, and may narrow the opening of the ultrasound beam.

For this reason, in ultrasound probe 20 according to this embodiment, buffer layer 400 is formed such that this buffer layer 400 is not in contact with transmission element 100. To be specific, buffer layer 400 according to this embodiment is provided apart from transmission element 100, in a region surrounding transmission element 100. Such a configuration is achieved, for example, by etching buffer layer 400 into a desired pattern after formation of buffer layer 400 in the step shown in FIG. 7C and before formation of the piezoelectric material for second piezoelectric body 202 in the step of FIG. 7D.

At this time, the position of buffer layer 400 is such that the line connecting the center position on the lower surface side of transmission element 100 and a position facing transmission element 100 at the upper end of buffer layer 400 forms 60 degrees or more with respect to the direction of transmission of the ultrasound beam from transmission element 100 (that is, the normal direction) (see angle θ in FIG. 8). As a result, a sufficient opening for the ultrasound beam emitted from transmission element 100 can be ensured.

As described above, with ultrasound probe 20 according to this embodiment, the phenomenon in which the vibration of transmission element 100 is hindered by buffer layer 400 can be suppressed. This leads to the improved transmission characteristic of transmission element 100.

Embodiment 3

The configuration of ultrasound probe 20 according to Embodiment 3 will now be described with reference to FIG.

Figure 9:
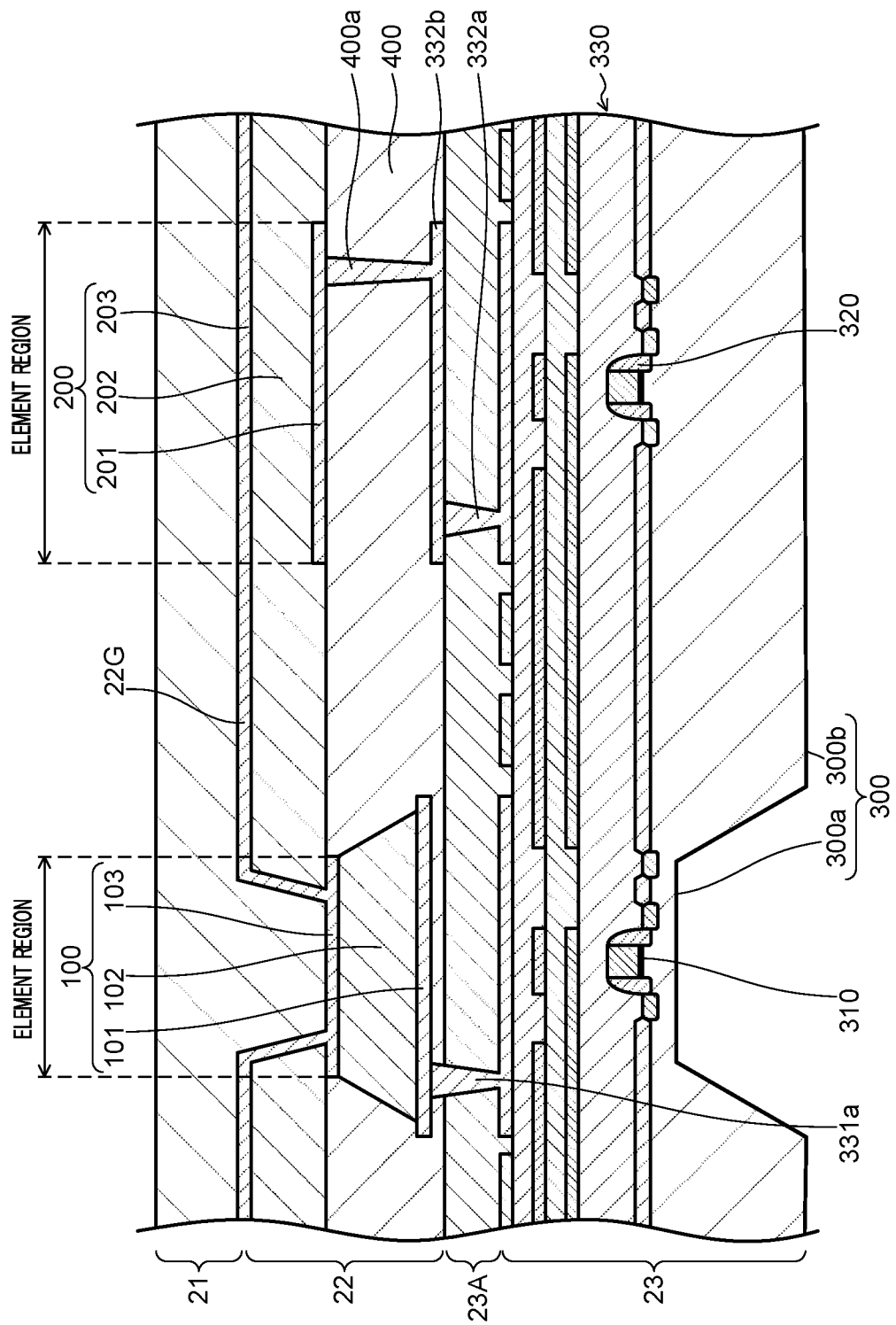
FIG. 9 is a sectional view showing the configuration of an ultrasound probe according to Embodiment 3.

9. FIG. 9 is a sectional view showing the configuration of ultrasound probe 20 according to Embodiment 3.

Ultrasound probe 20 according to this embodiment is different from Embodiment 1 in that thin buffer layer 400 is formed immediately below transmission element 100.

As described above, buffer layer 400 may hinder the flexural vibration of transmission element 100 and degrade the transmission characteristic of transmission element 100. However, since buffer layer 400 also functions as a backing member, considering suppression of reflection by circuit substrate 23, thin buffer layer 400 is also provided directly below transmission element 100 as necessary.

Such a configuration can be achieved, for example, by forming thin buffer layer 400 in the step shown in FIG. 7B, forming transmission element 100, and then forming buffer layer 400 again.

Other Embodiments

The present invention is not limited to the aforementioned embodiments and there are various potential modifications.

The aforementioned embodiments show the aspect in which a recess is provided only in the region immediately below transmission element 100 on the lower surface side of substrate 300. However, a recess may be provided in a region directly below reception element 200 on the lower surface side of substrate 300 such that the resonance frequency in the flexural vibration mode does not exist in the frequency band used for transmission/reception of ultrasound.

In the aforementioned embodiments, buffer layer 400 is formed by a printing method. However, depending on the material used for buffer layer 400, buffer layer 400 may be formed by a technique (for example, CVD) other than the printing method.

The aforementioned embodiments show the aspect in which buffer layer 400 is formed up to a position higher than the position of the upper end of transmission element 100. However, depending on how buffer layer 400 is formed, buffer layer 400 may be formed such that the position of the upper end of buffer layer 400 is lower than the position of the upper end of transmission element 100.

In the aforementioned embodiments, first piezoelectric body 102 of transmission element 100 is composed of PZT. However, an inorganic piezoelectric material other than PZT (for example, lead magnesium niobate titanate (PMN-PT) or lead zirconate magnesium niobate titanate (PMN-PZT)) may be used as first piezoelectric body 102.

In the above embodiment, second piezoelectric body 202 of reception element 200 is composed of PVDF. However, second piezoelectric body 202 may be composed of an organic piezoelectric material other than PVDF (for example, a urea resin). Second piezoelectric body 202 may have a single layer structure composed of only a piezoelectric material, or may have a laminated structure in which a metal or non-metal thin film layer is sandwiched between piezoelectric materials.

Specific examples of the present invention which have been described in detail above are merely illustrative and do not limit the scope of the claims The techniques described in the claims include various modifications and changes of the specific examples illustrated above.

INDUSTRIAL APPLICABILITY

The ultrasound probe according to the present disclosure can achieve high transmission/reception sensitivity over a wide frequency band.

REFERENCE SIGNS LIST

1 Ultrasound diagnostic apparatus
10 Ultrasound diagnostic apparatus body
11 Operation input section
12 Transmission section
13 Reception section
14 Image processing section
15 Display section
16 Control section
20 Ultrasound probe
21 Protective layer
22 Element array layer
22G Common electrode
23 Circuit substrate
23A Insulating layer
24 Backing member
30 Cable
100 Transmission element (first piezoelectric element)
101 First lower electrode
102 First piezoelectric body
103 First upper electrode
200 Reception element (second piezoelectric element)
201 Second lower electrode
202 Second piezoelectric body
203 Second upper electrode
300 Substrate
300a Thin film section
300b Thick film section
310 Transmission transistor
320 Reception transistor
330 Wiring layer
331a Through electrode
332a Through electrode
332b Wiring section
400 Buffer layer
400a Through electrode

What is claimed is:
1. An ultrasound probe, comprising:
a circuit substrate;
a buffer layer formed in a second region different from a first region of an upper surface of the circuit substrate and composed of an insulating material; and
an element array layer including a first piezoelectric element for ultrasound transmission formed in the first region of the circuit substrate without the buffer layer, and a second piezoelectric element for ultrasound reception formed in the second region of the circuit substrate on the buffer layer, wherein
the circuit substrate has a recess in a region of a lower surface thereof, the region corresponding to the first region,
the first piezoelectric element vibrates in a flexural vibration mode on the circuit substrate, and
the second piezoelectric element vibrates in a thickness vibration mode on the circuit substrate.
2. The ultrasound probe according to claim 1, wherein the buffer layer is an insulating material having a relative dielectric constant of 4 or less.
3. The ultrasound probe according to claim 1, wherein the buffer layer is formed of an organic material.
4. The ultrasound probe according to claim 3, wherein the buffer layer is formed of parylene, polyimide, polyethylene, or silicone rubber.

5. The ultrasound probe according to claim 1, wherein the buffer layer is formed of a material that satisfies Formula (1) below:

$$g2/g1 < 10 \quad \text{Formula (1)}$$

where g1 is an elastic modulus of a piezoelectric body of the second piezoelectric element, and g2 is an elastic modulus of the buffer layer.

6. The ultrasound probe according to claim 1, wherein the buffer layer is formed of a material satisfying Formula (2) below:

$$Z2/Z1 < 1 \quad \text{Formula (2)}$$

where Z1 is an acoustic impedance of a piezoelectric body of the second piezoelectric element, and Z2 is an acoustic impedance of the buffer layer.

7. The ultrasound probe according to claim 1, wherein a sum of a thickness of the second piezoelectric element and a thickness of the buffer layer satisfies Formula (3) below:

$$t \leq v/4f_{max} \quad \text{Formula (3)}$$

where t is the sum of the thickness of the second piezoelectric element and the thickness of the buffer layer; $f_{max}$ is a maximum frequency in a frequency band used for transmission/reception of ultrasound; and v is an average of a sound speed in the second piezoelectric element and a sound speed in the buffer layer.

8. The ultrasound probe according to claim 1, wherein the buffer layer surrounds a periphery of the first piezoelectric element, and is formed such that a position of an upper end of the buffer layer is higher than a position of an upper end of the first piezoelectric element.

9. The ultrasound probe according to claim 8, wherein the first piezoelectric element is not in contact with the buffer layer.

10. The ultrasound probe according to claim 1, wherein a thickness of the buffer layer is 2 um to 30 um both inclusive.

11. The ultrasound probe according to claim 1, wherein in the first piezoelectric element, a first lower electrode, a first piezoelectric body, and a first upper electrode are layered in this order from a side of the circuit substrate, in the second piezoelectric element, a second lower electrode, a second piezoelectric body, and a second upper electrode are layered in this order from the side of the circuit substrate, and the first piezoelectric body and the second piezoelectric body are composed of different materials.

12. The ultrasound probe according to claim 11, wherein the first piezoelectric body is formed of an inorganic piezoelectric material, and the second piezoelectric body is formed of an organic piezoelectric material.

13. The ultrasound probe according to claim 12, wherein the first piezoelectric body is formed of lead zirconate titanate (PZT).

14. The ultrasound probe according to claim 12, wherein the second piezoelectric body is formed of polyvinylidene fluoride (PVDF) resin.

15. An ultrasound diagnostic apparatus, comprising the ultrasound probe according to claim 1.

16. An ultrasound probe, comprising:
a circuit substrate;
a buffer layer that is formed of an insulating material, and has a first thickness in a first region of an upper surface of the circuit substrate and has a second thickness in a second region different from the first region, the second thickness being greater than the first thickness; and
an element array layer including a first piezoelectric element for ultrasound transmission formed in the first region of the circuit substrate on the buffer layer, and a second piezoelectric element for ultrasound reception formed in the second region of the circuit substrate on the buffer layer, wherein the circuit substrate has a recess in a region of a lower surface thereof, the region corresponding to the first region, the first piezoelectric element vibrates in a flexural vibration mode on the circuit substrate, and the second piezoelectric element vibrates in a thickness vibration mode on the circuit substrate.

* * * * *